United States Patent [19]

Curran et al.

[11] 4,160,094
[45] Jul. 3, 1979

[54] TETRAHYDROQUINOLINE DERIVATIVES

[75] Inventors: Adrian C. W. Curran, Newcastle-upon-Tyne; Roger Crossley, Reading; David G. Hill, Cookham, all of England

[73] Assignee: John Wyeth & Brother Limited, Maidenhead, United Kingdom

[21] Appl. No.: 550,903

[22] Filed: Feb. 18, 1975

Related U.S. Application Data

[63] Continuation-in-part of Ser. No. 460,265, Apr. 11, 1974, abandoned, which is a continuation-in-part of Ser. No. 403,289, Oct. 3, 1973, abandoned.

[51] Int. Cl.² .......................................... C07D 215/16
[52] U.S. Cl. ................................. 546/152; 424/274; 546/173
[58] Field of Search ..................... 260/283 R; 546/152

[56] References Cited

PUBLICATIONS

Curran et al., Chem. Abst., vol. 81, col. 37486m (1974).
Winterfeld et al., Chem. Abstr., vol. 67:73503j (1967).
Testor et al., Chem. Abst., vol. 59:9978b (1963).

Primary Examiner—Donald G. Daus
Assistant Examiner—Mary C. Lee
Attorney, Agent, or Firm—Arthur E. Wilfond

[57] ABSTRACT

The invention relates to new tetrahydroquinoline derivatives which are intermediates useful in the preparation of anti-ulcer agents. The new derivatives have formula (I)

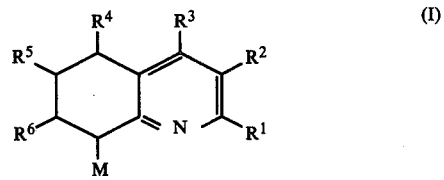

wherein M is sodium, potassium or lithium, $R^1$, $R^2$, $R^3$, $R^4$, $R^5$ and $R^6$ are the same or different and represent hydrogen, or a lower alkyl, or a phenyl radical, and any of $R^4$, $R^5$ and $R^6$ may be a gem-di-lower alkyl radical.

12 Claims, No Drawings

TETRAHYDROQUINOLINE DERIVATIVES

The invention relates to novel tetrahydroquinoline derivatives and to processes for preparing them. This application is a continuation-in-part of our copending U.S. Ser. No. 460,265 filed Apr. 11, 1974, now abandoned, which in turn is a continuation-in-part of our U.S. Application Ser. No. 403,289 filed 3rd Oct., 1973 and now abandoned.

The invention provides novel metal compounds of formula I

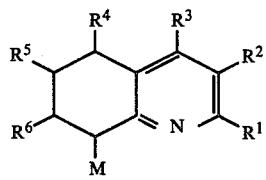

wherein M is sodium, potassium or lithium, $R^1$, $R^2$, $R^3$, $R^4$, $R^5$ and $R^6$ are the same or different and represent hydrogen or lower alkyl, or phenyl radicals and any of $R^4$, $R^5$ and $R^6$ may be a gem-dilower alkyl radical. The lower alkyl radical may be a straight or branched chain, having from 1 to 6 carbon atoms, e.g. methyl, ethyl, n-, and iso-propyl and n-, s and t- butyl, and when any of $R^4$, $R^5$ and $R^6$ is a gem-dilower alkyl radical it is preferably a gem-dimethyl group. The term alkyl radical is also intended to embrace cyclic alkyl radicals e.g. cyclobutyl, cyclopentyl and cyclohexyl.

Particularly preferred compounds are those in which one of $R^1$, $R^2$, $R^3$, $R^4$, $R^5$ and $R^6$ is methyl and the others are hydrogen. The preferred compounds of formula I are those in which M is lithium.

Thus the present invention provides, in one preferred aspect a compound of formula II

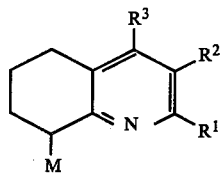

wherein $R^1$, $R^2$ and $R^3$ are selected from hydrogen and methyl and M is as defined above.

The novel metal compounds of formula I are intermediates for preparing anti-ulcer agents by methods described in our U.S. Ser. No. 460,265 and also U.S. Ser. No. 526,354, filed Nov. 22, 1974, inventor A. C. Curran and U.S. Ser. No. 526,565, filed Nov. 25, 1974, inventors Curran and Shepherd. The novel metal compounds are generally used in situ. For instance in the processes of our U.S. Ser. No. 460,265 they may be treated with carbon dioxide to give the corresponding metal salts of the 5,6,7,8-tetrahydroquinoline 8-carboxylic acids which in turn may be converted to the corresponding lower alkyl 5,6,7,8-tetrahydroquinoline 8-carboxylates by treatment with a lower alkanol in the presence of an acidic catalyst. After that the lower alkyl ester may be converted to the corresponding 8-thiocarboxamides which are anti ulcer agents.

The invention includes a process of preparing the novel metal derivatives, by treating a corresponding compound in which M is hydrogen, with a metal alkyl. The metal alkyl may be of formula $MR^{10}$ wherein M is sodium, potassium or lithium and $R^{10}$ is lower alkyl, aryl or aryl lower alkyl. The metal compounds obtained may be converted to the corresponding carboxylic acids by treatment of the product in situ with carbon dioxide, conveniently by bubbling $CO_2$ gas into the reaction mixture. The resulting compound of formula I in which M is $CO_2H$ is obtained (usually as an acid addition salt) by treatment of the product, a metal salt of a compound of formula I in which M is COOH, with acid e.g. hydrochloric or hydrobromic acid. A convenient method is to treat a solution of the salt with conc. hydrochloric acid or gaseous hydrogen chloride. A convenient reagent $MR^{10}$ is phenyl lithium or n-butyl lithium. $R^{10}$ may have any of the values given above for the lower alkyl radical $R^1$, $R^2$, $R^3$, $R^4$, $R^5$ and $R^6$. The aryl radical is preferably phenyl, and the aryl lower alkyl radical may be one in which the lower alkyl portion has any of the lower alkyl values discussed above and the aryl radical is preferably phenyl.

It has been found that when a compound of formula I in which $R^1$ is methyl and $R^2$, $R^3$, $R^4$, $R^5$ and $R^6$ are hydrogen and M is hydrogen is treated with metal alkyl the metal atom may be inserted either at the desired position or in the methyl group $R^1$. This side reaction may also occur with any compound containing an alkyl group $R^1$ in which there are one or two hydrogen atoms on the carbon atom adjacent to the pyridine ring. When such compounds are being used in the preparation of the anti-ulcer derivatives the metal derivatives are not separated at this stage but are subjected to subsequent stages, the desired derivatives being separated later.

The metal derivatives may be reacted with alkylsilyl isothiocyanates as described in the U.S. Ser. No. 526,565, filed Nov. 25, 1974 (inventors A. C. Curran and R. G. Shepherd) or with alkyl isothiocyanates as described in U.S. Ser. No. 526,354, filed Nov. 22, 1974 (inventor A. C. Curran). The by products discussed in the previous paragraph which contain a metal atom in an alkyl group $R^1$ do not normally react with alkyl-silyl isothiocyanates.

The compounds of formula I are usually prepared in a dry organic solvent e.g. an ether such as diethyl ether, dimethoxy ethane or tetrahydrofuran, or a hydrocarbon solvent e.g. benzene or hexane.

If an ether is used as a solvent it may be necessary to remove it prior to subsequent reaction of the metal Compound I.

The metal derivatives of formula I generally exhibit an intense colour in solution, usually red or reddish orange.

The following Examples illustrate the invention; all temperatures are in °C.:

EXAMPLE 1

8-Lithio-2-phenyl-5,6,7,8-tetrahydroquinoline

A solution of 2-phenyl-5,6,7,8-tetrahydroquinoline (20 g.) in ether (50 ml.) was added dropwise over 30 mins. to a preformed ethereal solution of phenyllithium (prepared from bromobenzene (40 g.) and lithium (2.78 g.) in dry ether (160 ml.). The reaction mixture was stirred for 1 hour at room temperature and the obtained 8-lithio-2-phenyl-5,6,7,8-tetrahydroquinoline treated in situ with dry $CO_2$ gas until the red colour was discharged. The solvent was removed in vacuo and the residue dissolved in ethanol saturated with dry HCl gas (250 ml.) and the solid filtered and recrystallised from water giving 2-phenyl-5,6,7,8-tetrahydroquinoline-8-carboxylic acid hydrochloride (12 g.). This was converted to the corresponding methyl ester by dissolving in methanol (200 ml.) and treating the methanol solution with dry HCl gas whilst heating under reflux for 4 hours as described in our copending application U.S. Ser. No. 460,265.

EXAMPLE 2

8-Lithio-5,6,7,8-tetrahydroquinoline

A solution of 5,6,7,8-tetrahydroquinoline (14 g.) in dry ether (100 ml.) was added dropwise over ½ hour to an ethereal solution of phenyl lithium (prepared from bromobenzene (42 g.) and lithium (3.7 g.) in dry ether (300 ml.) and the reaction mixture stirred at room temperature for a further one hour. The cooled reaction mixture containing 8-lithio-5,6,7,8-tetrahydroquinoline was saturated with dry $CO_2$ gas, evaporated in vacuo and the residue treated with methanol previously saturated with dry HCl (500 ml.) giving methyl-5,6,7,8-tetrahydroquinoline-8-carboxylate as described in our copending U.S. Ser. No. 460,265.

EXAMPLE 3

2-t-butyl[8-lithio]-5,6,7,8-tetrahydroquinoline 2-t-Butyl-5,6,7,8-tetrahydroquinoline (18.9 g., 0.1 m). was treated with phenyl lithium (0.1 m.) by the general method described in Example 1 to obtain 2-t-butyl[8-Lithio]-5,6,7,8-tetrahydroquinoline which was treated in situ with $CO_2$ and the product converted to methyl-2-t-butyl-5,6,7,8-tetrahydroquinoline-8-carboxylate by refluxing in methanol saturated with dry HCl gas as described in our copending U.S. Ser. No. 460265.

EXAMPLE 4

8-Lithio-2-methyl-5,6,7,8-tetrahydroquinoline

Reaction of 2-methyl-5,6,7,8-tetrahydroquinoline with phenyl lithium following the method of Example 1 gave 8-lithio-2-methyl-5,6,7,8-tetrahydroquinoline and 2-lithiomethyl-5,6,7,8-tetrahydroquinoline which were treated in situ with carbon dioxide followed by esterification of the product by refluxing in methanol saturated with dry HCl gas according to the general method described in our copending U.S. Ser. No. 460,265.

EXAMPLE 5

8-Lithio-3-methyl-5,6,7,8-tetrahydroquinoline n-Butylbromide (285 ml.) in dry ether (500 ml.) was added to clean lithium wire (42 g., 6 m) in dry ether (1 l.) with external cooling (−40° C.) under nitrogen at such a rate to maintain an internal temperature of −15° C. Upon completion of the addition the reaction mixture was stirred until the temperature rose to 10° C. (approx. 2 hours). The concentration of butyl lithium was calculated by standardising against N/10 HCl and the quantity of 3-methyl-5,6,7,8-tetrahydroquinoline required in the next stage adjusted to have a 1.2 m excess of butyl lithium.

A stirred solution of 3-methyl-5,6,7,8-tetrahydroquinoline (147 g., 1 m) in dry ether (700 ml.) was treated with a freshly prepared solution of butyl lithium (860 ml. of a 1.4 M solution i.e. 1.2 m) under nitrogen. The reaction mixture was stirred for an additional 15 min. The resulting 8-lithio-3-methyl-5,6,7,8-tetrahydroquinoline was treated in situ with a slow stream of dry $CO_2$ gas which was bubbled into the reaction mixture until it became colourless. The reaction mixture was processed as described in Example 19 of our copending U.S. Ser. No. 460,265 to give methyl-3-methyl-5,6,7,8-tetrahydroquinoline-8-carboxylate.

EXAMPLE 6

8-Lithio-3-methyl-5,6,7,8-tetrahydroquinoline

A 3-necked flask is charged with 3-methyl-5,6,7,8-tetrahydroquinoline (45 g. 0.29 moles) and ether (400 ml). Phenyl lithium solution (330 ml. of a 1 molar solution 0.3 moles in ether is added to the stirred solution at a rate to give gentle reflux. Reflux is maintained for 2 hours. After cooling in an ice-bath $CO_2$ is bubbled through the resulting red solution of 8-lithio-3-methyl-5,6,7,8-tetrahydroquinoline till no further colour change. The mixture is further treated with methanolic HCl as described in Example 24 of copending U.S. Ser. No. 460,265 to give methyl-3-methyl-5,6,7,8-tetrahydroquinoline-8-carboxylate.

EXAMPLE 7

8-Lithio-3-methyl-5,6,7,8-tetrahydroquinoline

A solution of 15% w/w n-butyl lithium in hexane (51 ml.) ca. 0.12 m) was added portionwise to a solution of 3-methyl-5,6,7,8-tetrahydroquinoline (14.7 g., 0.1 m) in ether (100 ml.) and the mixture allowed to stand at room temperature for 1 hour to form 8-lithio-3-methyl-5,6,7,8-tetrahydroquinoline. The solution was then added dropwise to a cooled, stirred solution of methylchloroformate (9.45 g., 0.1 m) in ether (100 ml.). The mixture was further treated as described in Example 25 of copending U.S. Ser. No. 460,265 to give methyl-3-methyl-5,6,7,8-tetrahydroquinoline-8-carboxylate.

EXAMPLE 8

8-Lithio-3,7,7-trimethyl-5,6,7,8-tetrahydroquinoline 3,7,7-Trimethyl-5,6,7,8-tetrahydroquinoline (17.5 g, 0.1 m) was dissolved in dry ether (200 ml.) and treated with a solution of n-butyl lithium in hexane (15% w/w solution, 56 ml.) under nitrogen. The reaction mixture containing 8-lithio-3,7,7-trimethyl-5,6,7,8-tetrahydroquinoline was allowed to stand at room temperature for 30 minutes and then treated with $CO_2$ gas until the intense red colour was discharged. The reaction mixture was further treated as described in Example 36 of our copending U.S. Ser. No. 460,265 to give methyl-3,7,7-trimethyl-5,6,7,8-tetrahydroquinoline-8-carboxylate.

EXAMPLE 9

8-Lithio-3-methyl-5,6,7,8-tetrahydroquinoline

To a solution of 3-methyl-5,6,7,8-tetrahydroquinoline (10 g; 0.068 m.) in dry hexane (50 ml.) was added 50 ml. of a 15% w/w solution of n-butyl lithium in hexane (0.09 m.) dropwise with stirring under an atmosphere of nitrogen. The resulting dark red solution of 8-lithio-3-methyl-5,6,7,8-tetrahydroquinoline was stirred for 15 minutes at room temperature and then treated with carbon disulphide (10 ml.). The resulting pale yellow suspension was poured into water (100 ml.) and the aqueous solution was washed with ether (3×100 ml.).

The aqueous solution of the lithium salt of 3-methyl-5,6,7,8-tetrahydroquinoline-8-dithiocarboxylic acid was converted to 3-methyl-5,6,7,8-tetrahydroquinoline-8-thiocarboxamide as described in Example 37 of our copending U.S. Ser. No. 460,265.

EXAMPLE 10

8-Lithio-4-methyl-5,6,7,8-tetrahydroquinoline

A solution of 4-methyl-5,6,7,8-tetrahydroquinoline (5.83 g., 0.04 mole) in dry benzene (40 ml.) was cooled to 0° and to the stirred solution was added dropwise a 15% w/w solution of butyl lithium in hexane (17.5 ml., 0.04 mole) under an atmosphere of nitrogen. The red reaction mixture of 8-lithio-4-methyl-5,6,7,8-tetrahydroquinoline was stirred at 0° for a further 30 minutes. It can then be treated with carbon dioxide followed by methanolic HCl to obtain methyl-4-methyl-5,6,7,8-tetrahydroquinoline-8-carboxylate which can be converted to 4-methyl-5,6,7,8-tetrahydroquinoline-8-thiocarboxamide by the procedures described in copending U.S. Ser. No. 460,265.

EXAMPLE 11

8-Lithio-3-methyl-5,6,7,8-tetrahydroquinoline

A solution of n-butyl lithium in hexane (15% w/w, 7 ml, 0.01 mole) was added to a stirred solution of 3-methyl-5,6,7,8-tetrahydroquinoline (1.47 g. 0.01 mole) in dry ether (25 ml.). The mixture was stirred at room temperature for 20 min. and then to the 8-lithio-3-methyl-5,6,7,8-tetrahydroquinoline. $D_2O$ (1 ml.) was added when the intense anion colouration disappeared. The stirring was continued for 5 min. then anhydrous magnesium sulphate was added and the solution was filtered and evaporated to give 8-deutero-3-methyl-5,6,7,8-tetrahydroquinoline (1.4 g., 96%). G.l.c. 10% MS200 150° 99% at 4 min., infra-red spectrum max. 2100 2200 cm$^{-1}$ (C-D stretch)., n.m.r. spectrum indicates >90% replacement of lithium by deuterium at C-8.

In the presence of $NaOD/D_2O$, 3-methyl-5,6,7,8-tetrahydroquinoline does not incorporate deuterium over a period of 2 h. The incorporation observed above therefore cannot be as a result of base-catalysed exchange.

EXAMPLE 12

8-Lithio-5,6,7,8-tetrahydroquinoline

The title compound is prepared using n-butyl lithium (9% w/v in hexane) and 5,6,7,8-tetrahydroquinoline by the general procedure of Example 7. The product may be converted to 5,6,7,8-tetrahydroquinoline-8-thiocarboxamide by the procedures described in Example 2 above, and U.S. Ser. No. 460,265.

EXAMPLE 13

2-Ethyl-8-lithio-5,6,7,8-tetrahydroquinoline

By the method described in Example 7 using n-butyl lithium solution (9% w/v, 10 ml, 0.014 mol), and 2-ethyl-5,6,7,8-tetrahydroquinoline (2.3 g, 0.014 mol) and title compound is prepared and converted in situ to methyl 2-ethyl-5,6,7,8-tetrahydroquinoline-8-carboxylate which was converted to the corresponding 8-thioamide by the procedure described in U.S. Ser. No. 460,265.

EXAMPLE 14

2-n-butyl-8-lithio-5,6,7,8-tetrahydroquinoline

By the method described in Example 7 using n-butyl lithium solution (9% w/v, 13.5 g, 0.03 mol) and 2-n-butyl-5,6,7,8-tetrahydroquinoline (6 g., 0.03 mol) the title compound is prepared and converted in situ to methyl 2-n-butyl-5,6,7,8-tetrahydroquinoline-8-carboxylate and then to the corresponding 8-thioamide by the procedure described in U.S. Ser. No. 460,265.

EXAMPLE 15

8-Lithio-2-methyl-4-phenyl-5,6,7,8-tetrahydroquinoline

By the method described in Example 7 using n-butyl lithium solution (9% w/v, 57 ml, 0.077 mol), and 2-methyl-4-phenyl-5,6,7,8-tetrahydroquinoline, the title compound is prepared and converted in situ to methyl 2-methyl-4-phenyl-5,6,7,8-tetrahydroquinoline-8-carboxylate and then to the corresponding 8-thioamide by the procedure described in U.S. Ser. No. 460,265.

EXAMPLE 16

8-Lithio-3,4-dimethyl-5,6,7,8-tetrahydroquinoline

By the method described in Example 7 using n-butyl lithium solution (9% w/v, 25 ml, 0.034 mol), and 3,4-dimethyl-5,6,7,8-tetrahydroquinoline-(5.65 g, 0.034 mol) the title compound is prepared and converted to methyl 3,4-dimethyl-5,6,7,8-tetrahydroquinoline-8-carboxylate which is then converted to the corresponding 8-thioamide by the procedure of U.S. Ser. No. 460,265.

EXAMPLE 17

8-Lithio-3-methyl-5,6,7,8-tetrahydroquinoline

To a solution of 3-methyl-5,6,7,8-tetrahydroquinoline (10 g) in anhydrous ether (50 ml) was added dropwise with stirring under nitrogen a 1.67 molar solution of methyllithium (40 ml.). The stirring was continued for ½ hour then the dark red solution of 8-lithio-3-methyl-5,6,7,8-tetrahydroquinoline was treated with a brisk stream of $CO_2$ gas until the suspension became pale yellow. The resulting 3-methyl-5,6,7,8-tetrahydroquinoline-8-carboxylic acid lithium salt was processed in the manner described in copending application U.S. Ser. No. 460,265 to give methyl-3-methyl-5,6,7,8-tetrahydroquinoline-8-carboxylate.

EXAMPLE 18

8-Lithio-3-methyl-5,6,7,8-tetrahydroquinoline

A solution of n-butyl-lithium (15% w/w, 36 ml, 0.05 mole) in hexane was added portionwise to a stirred solution of 3-methyl-5,6,7,8-tetrahydroquinoline (7.3 g, 0.05 mole) in dry tetrahydrofuran (50 ml.) at 0° under nitrogen. After the addition the solution was stirred for 0.5 hour to give a dark red solution of 8-lithio-3-methyl-5,6,7,8-tetrahydroquinoline.

EXAMPLE 19

3-Methyl-8-sodio-5,6,7,8-tetrahydroquinoline

A stirred suspension of sodium sand (4.6 g, 0.2 mole) in petroleum ether (b.p. 40°-60° C.) was treated over 1.5 hour under an atmosphere of nitrogen with chlorobenzene (11.3 g, 0.1 mole) maintaining an internal temperature of 25° C. by external cooling. When the addition was complete the mixture was stirred for a further 2 hours to complete the formation of phenyl-sodium. The resulting mixture is cooled to 0° C. and treated with 3-methyl-5,6,7,8-tetrahydroquinoline (14.7 g, 0.1 mole) which was added portionwise producing, after stirring for 0.5 hour, a solution of 3-methyl-8-sodio-5,6,7,8-tetrahydroquinoline.

EXAMPLE 20

Following the procedure of Example 5 but substituting the indicated tetrahydroquinolines for 3-methyl 5,6,7,8-tetrahydroquinoline the indicated lithium derivatives are prepared and converted to the corresponding methyl-5,6,7,8-tetrahydroquinoline-8-carboxylates.

| 5,6,7,8-tetrahydroquinoline (THQ) derivative | | |
|---|---|---|
| Starting material | lithium derivative | methyl ester |
| 3-n-butyl-THQ | 3-n-butyl-8-lithio-THQ | methyl-3-n-butyl-THQ-8 carboxylate |
| 3-n-pentyl-THQ | 8-lithio-3-n-pentyl-THQ | methyl-3-n-pentyl-THQ-8-carboxylate |
| 3,5-dimethyl-THQ | 3,5-dimethyl-8-lithio-THQ | methyl-3,5-dimethyl THQ-8-carboxylate |
| 3,6-dimethyl-THQ | 3,6-dimethyl-8-lithio-THQ | methyl-3,6-dimethyl THQ-8-carboxylate |
| 3,7-dimethyl-THQ | 3,7-dimethyl-8-lithio-THQ | methyl-3,7-dimethyl THQ-8-carboxylate |
| 3-methyl-5n-butyl THQ | 3-methyl-5n-butyl-8-lithio THQ | methyl-3-methyl-5-n-butyl-THQ-8-carboxylate |
| 3-methyl-6-iso-propyl | 3-methyl-6-iso-propyl-8-lithio-THQ | methyl-3-methyl-6-isopropyl-THQ-8-carboxylate |
| 4-n-hexyl-THQ | 4-n-hexyl-8-lithio-THQ | methyl-4-n-hexyl-THQ-8-carboxylate |
| 5-methyl-THQ | 8-lithio-5-methyl-THQ | methyl-5-methyl-THQ-8-carboxylate |
| 6-ethyl-THQ | 6-ethyl-8-lithio-THQ | methyl-6-ethyl-THQ-8-carboxylate |
| 7-n-propyl-THQ | 8-lithio-7-n-propyl-THQ | methyl-7-n-propyl-THQ-8-carboxylate |

We claim:
1. An organic solution of a compound of formula

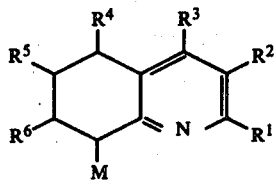

wherein M is sodium, potassium or lithium, $R^1$, $R^2$, $R^3$, $R^4$, $R^5$ and $R^6$ are the same or different and represent hydrogen or a lower alkyl group of 1–6 carbon atoms, with the proviso that when any two of $R^1$, $R^2$ and $R^3$ or $R^4$, $R^5$ and $R^6$ are present on adjacent carbon atoms and are both lower alkyl, they are selected from normal and secondary alkyl groups.

2. A solution as claimed in claim 1 wherein $R^1$, $R^2$, $R^3$, $R^4$, $R^5$ and $R^6$ are selected from hydrogen and methyl.

3. A solution of a compound as claimed in claim 2 wherein $R^1$, $R^3$, $R^4$, $R^5$ and $R^6$ are hydrogen and $R^2$ is methyl.

4. A solution as claimed in claim 2 wherein the compound is 8-lithio-5,6,7,8-tetrahydroquinoline.

5. A solution as claimed in claim 1 wherein the compound is 2-t-butyl-8-lithio-5,6,7,8-tetrahydroquinoline.

6. A solution as claimed in claim 2 wherein the compound is 8-lithio-2-methyl-5,6,7,8-tetrahydroquinoline.

7. A solution as claimed in claim 2 wherein the compound is 8-lithio-3-methyl-5,6,7,8-tetrahydroquinoline.

8. A solution as claimed in claim 2 wherein the compound is 8-lithio-4-methyl-5,6,7,8-tetrahydroquinoline.

9. A solution as claimed in claim 1 wherein the compound is 2-ethyl-8-lithio-5,6,7,8-tetrahydroquinoline.

10. A solution as claimed in claim 1 wherein the compound is 2-n-butyl-8-lithio-5,6,7,8-tetrahydroquinoline.

11. A solution as claimed in claim 2 wherein the compound is 8-lithio-3,4-dimethyl-5,6,7,8-tetrahydroquinoline.

12. A solution as claimed in claim 2 wherein the compound is 3-methyl-8-sodio-5,6,7,8-tetrahydroquinoline.

* * * * *